United States Patent [19]
Schulman et al.

[11] Patent Number: 6,035,237
[45] Date of Patent: Mar. 7, 2000

[54] IMPLANTABLE STIMULATOR THAT PREVENTS DC CURRENT FLOW WITHOUT THE USE OF DISCRETE OUTPUT COUPLING CAPACITORS

[75] Inventors: Joseph H. Schulman, Santa Clarita; Alfred E. Mann, Beverly Hills; John C. Gord, Venice; Ronald J. Lebel, Sherman Oaks, all of Calif.

[73] Assignee: Alfred E. Mann Foundation, Valencia, Calif.

[21] Appl. No.: 08/447,455

[22] Filed: May 23, 1995

[51] Int. Cl.[7] ............................... A61N 1/32; A61N 1/16
[52] U.S. Cl. ................... 607/63; 607/2; 607/37; 607/57
[58] Field of Search ............... 607/2, 5, 37, 57, 607/63

[56] References Cited

U.S. PATENT DOCUMENTS 5,312,444  5/1994  Bocek et al. ........................... 607/5
5,531,774  7/1996  Schulman et al. ..................... 607/57

*Primary Examiner*—William E. Kamm
*Assistant Examiner*—Carl H. Layno
*Attorney, Agent, or Firm*—Abraham N. Seidman

[57] ABSTRACT

An implantable living tissue stimulator avoids the use of conventional coupling capacitors in its output stage, yet still prevents an average dc current flow from flowing through living tissue in electrical contact with the stimulator. The output stage generates and applies a biphasic stimulating current pulse to selected paired output terminals. The terminals, in turn, are electrically connected to respective electrodes which are positioned so as to contact the living tissue to be stimulated. In one embodiment, special circuitry is employed within the output stage to block dc current flow through the living tissue and to balance the electrical charge that is delivered to the living tissue. In another embodiment, the electrodes themselves are made from a material that allows them to function as a capacitor. In yet an additional embodiment, the coupling capacitors are integrated into the leads that connect the output terminals of the output stage with the electrodes.

38 Claims, 8 Drawing Sheets

IMPLANTABLE STIMULATOR THAT PREVENTS DC CURRENT FLOW WITHOUT THE USE OF DISCRETE OUTPUT COUPLING CAPACITORS

BACKGROUND OF THE INVENTION

The present invention relates to implantable living tissue stimulators, such as neural stimulators or cochlear stimulators, that do not use output coupling capacitors. More particularly, the invention relates to circuit designs and methods for use within the output stage of such stimulators that prevent the flow of dc current between paired electrodes.

Most implantable living tissue stimulators employ coupling capacitors to provide dc isolation between the output stage of such devices and the tissue-stimulating electrodes. A dc current flow through living tissue can be very undesirable, particularly when allowed to continue over prolonged periods of time. This is because prolonged dc current flow through living tissue can cause tissue growth at one of the electrodes, and tissue destruction at the other electrode, and can also cause excessive repeated firing of muscle neuron tissue. Hence, except for certain tissue growth and tissue healing devices, coupling capacitors are normally used to block all dc current flow. Such capacitors advantageously allow an ac current to flow through and stimulate the living tissue, such as a biphasic current pulse, but prevent any undesirable dc current flow in the tissue. More particularly, such capacitors limit the coulombs that are allowed to flow in one direction (where coulomb flow per unit time in one direction is the electrical definition of dc current).

Unfortunately, the output coupling capacitors used within a living tissue stimulator may represent a significant portion of the total volume of the device, ofttimes occupying much more volume than the integrated circuit chip which contains all of the stimulating circuitry. This is particularly the case when the stimulator is a multichannel stimulator, employing e.g., 16 electrodes, and hence at least 16 coupling capacitors, as is common with implantable cochlear stimulators. In order to reduce the overall volume and size of a living-tissue stimulator device, it would therefore be desirable to avoid the use of output coupling capacitors. However, if coupling capacitors are not used, then there is a need for other means associated with the implant device to assure that no dc current flows through the electrodes.

The present invention addresses the above and other needs.

SUMMARY OF THE INVENTION

The present invention prevents dc current flow (i.e., unidirectional coulomb flow) between paired electrodes of an implantable living-tissue stimulator, without the use of discrete output coupling capacitors within the stimulator circuitry, in one of two ways. First, special circuitry is employed within the output stage of the chip on which the stimulating circuitry is placed (or in a second chip) that monitors the current flow through the electrodes and forces such current flow to always assume an average zero dc value. Second, coupling capacitors may be integrated into the electrodes of an electrode array, or into the leads connecting the electrode array to the stimulator circuitry, thereby removing the bulky coupling capacitors from the package containing the stimulating chip.

It is noted that the two dc-current-prevention measures summarized above are not mutually exclusive. Rather, one or both may be used for a given application.

In accordance with the first way mentioned above—using special circuitry as part of the output stage that prevents dc current flow—there are at least four different types of circuits that may be used: (1) a circuit that simulates a capacitor; (2) a circuit that monitors and balances the current flow (so that, e.g., each negative current pulse is followed by an equal positive current pulse); (3) a circuit that looks for non-biphasic pulses and makes them biphasic; or (4) a circuit that senses average dc current flow and cancels it with a current of equal and opposite polarity.

In accordance with the second way mentioned above—integrating coupling capacitors into the electrode array—the present invention removes the coupling capacitors from inside of the implanted package or housing wherein the stimulator circuitry resides and places them within the lead/electrode array, e.g., as part of the lead connecting the output stage with the electrodes, or as part of the electrode itself. One way to incorporate the coupling capacitor as part of the electrode itself is to make each electrode effectively function as one-half of a capacitor. For example, the electrodes may be made from sintered anodized tantalum having dimensions of, e.g., approximately 0.002×0.040×0.020 inches. The two electrodes that are paired together, and between which a stimulating current pulse is to flow, then function as the two plates of a capacitor, with the anodized layer on the electrodes functioning as the dielectric of the capacitor. Such a "capacitor" (e.g., having "plates" of approximately the above dimensions and an appropriate spacing therebetween) has a capacitance of around 0.1 μfd. Each plate of sintered tantalum acts as a capacitor for current flow in one direction and as a short for current flow in the other direction, thereby functioning as a polarized capacitor. However, with sintered tantalum placed on both electrodes, the pair of electrodes combine to act as a single bipolar capacitor.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

It is noted that the present invention has applicability to a wide range of different types of living tissue stimulators, e.g., cochlear stimulators, functional electrical stimulators (FES), muscle/organ stimulators, functional neural stimulators (FNS), and the like. Representative stimulators, electrode arrays, and associated components with which the present invention may be used are described, e.g., in the following U.S. Patent documents: U.S. Pat. Nos. 4,592,359; 4,918,745; 4,947,844; 4,991,582; 4,969,468; and 5,193,539; 5,193,540; and U.S. patent application Ser. No. 08/322,066, filed Oct. 12, 1984 (assigned to the same assignee as the present application), all of which patent documents are incorporated herein by reference.

Living tissue stimulators with which the present invention may be used include single or multichannel stimulators adapted to provide an electrical stimulation current between pairs of electrodes configured in monopolar, bipolar, or multipolar electrode schemes. Each of these stimulators employs some type of output stage that generates the stimulation current and applies it to a selected pair of electrodes.

Figure 1:
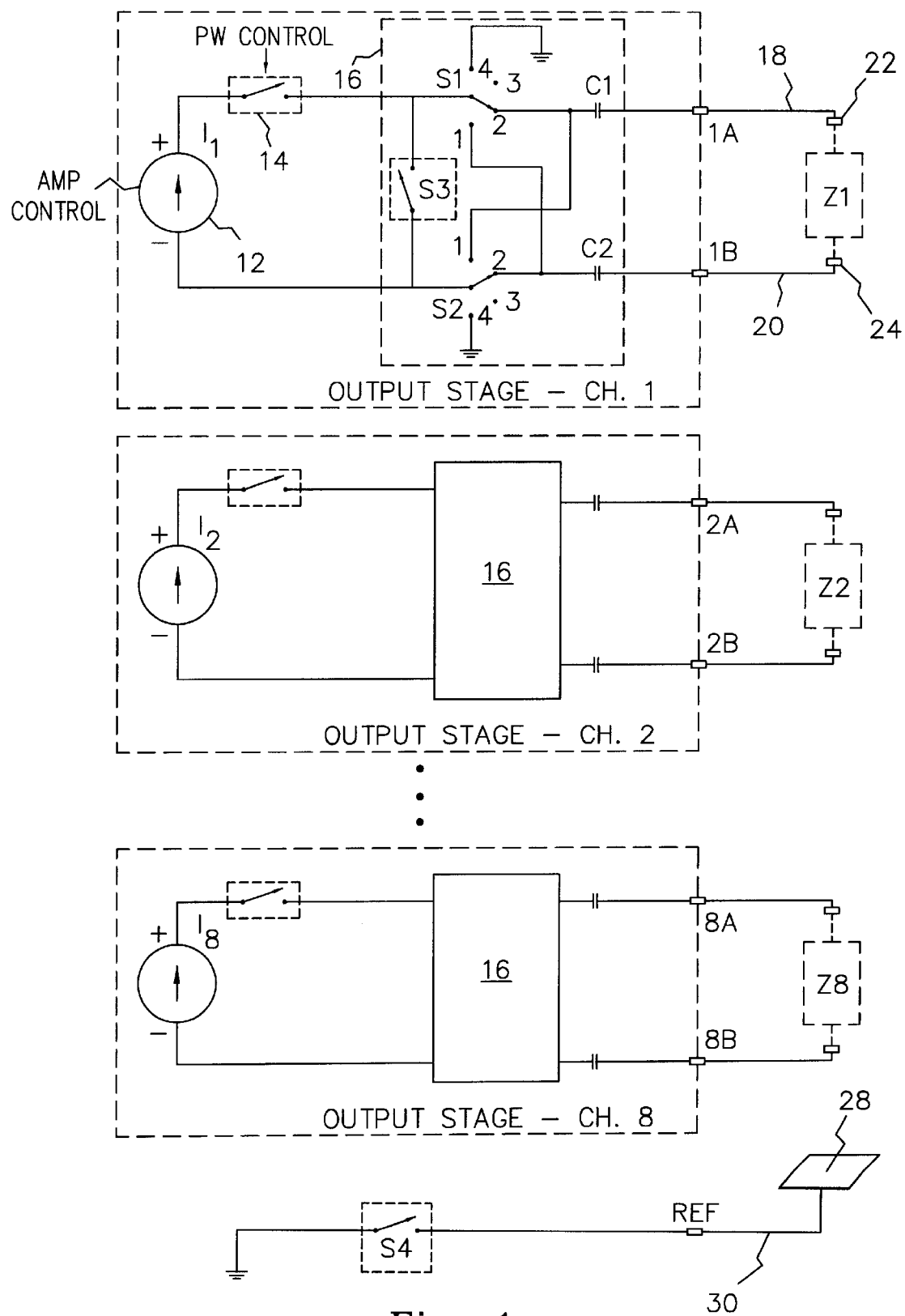
FIG. 1 shows a functional electrical schematic diagram of the output stage of an eight channel implantable stimulator that can stimulate through up to 17 electrodes.

The output stage of a typical eight channel stimulator is illustrated in the schematic diagram of FIG. 1. As seen in FIG. 1, eight identical output stages are employed. Each channel includes a single polarity current generator 12, a pulse switch 14, a switch matrix 16 (containing three switches S1, S2 and S3), two output terminals "A" and "B", and two coupling capacitors C1 and C2 that connect the switch matrix 16 to the two output terminals "A" and "B", respectively. The "A" and "B" output terminals, in turn, are connected through respective conductors 18 and 20 to electrodes 22 and 24. The electrodes 22 and 24 are positioned such that body tissue, represented by the box Z1, provides a current path through which the stimulating current flows as it passes between electrodes.

The eight output stages of FIG. 1 are further enhanced with a common reference terminal, REF, selectively connected to the current source of each output stage through switch S4 and the switch matrix 16. The switch matrix 16 connects the REF terminal to the "+" or "−" terminals of the current sources of the output stages, or disconnects (floats) the REF terminal from the current sources. A reference (or indifferent) electrode 28 is also available for unipolar stimulation and is connected to the REF terminal through a conductor 30.

The switch matrix 16 of each output stage allows each polarity ("+" or "−") of the current source to be connected either OFF, to terminal A, to terminal B, or to the REF terminal. This allows all stimulation modes, unipolar A, unipolar B, and bipolar, to be connected to the two "A" and "B" electrodes of each respective output stage, as summarized in Table 1.

TABLE 1

| Stimulation | S1 position | S2 position | Polarity U = Unipolar (S4clad) Bi = Bipolar (S4open) |
|---|---|---|---|
| OFF | 3 | 3 | OFF |
| Bipolar + | 2 | 2 | Bi(A+) (B−) |
| Bipolar − | 1 | 1 | Bi(A−) (B+) |
| Unipolar A+ | 2 | 4 | U(A+), B(off) |
| Unipolar A− | 4 | 1 | U(A−), B(off) |
| Unipolar B+ | 1 | 4 | U(B+), A(off) |
| Unipolar B− | 4 | 2 | U(B−), A(off) |

By selectively opening switch S4 (so that the reference electrode 28 floats), and through appropriate control of the switches S1, S2 and S3 within the switch matrix 16, it is thus possible to achieve multipolar stimulation. Multipolar stimulation occurs when current is applied between one electrode of one output stage and another electrode of another output stage. Multipolar stimulation could occur, e.g., between terminal 1B of the channel 1 output stage and terminal 8A of the channel 8 output stage.

Note, in accordance with the present invention, switch S3 is necessary for biphasic stimulation. By closing switch S3 between biphasic pulses, the dc excess charge due to pulse non-symmetry can be cancelled out. That is, it is not possible to make a perfectly balanced biphasic pulse. The slight error in a coulomb mismatch between the positive and negative charges will eventually build up to block the output. Switch S3 thus prevents this buildup by discharging the output coupling capacitors, whether discrete coupling capacitors included within the circuit package, or capacitors that form an integral part of the electrode/lead.

The coupling capacitors C1 and C2 advantageously prevent any dc current from flowing through the tissue load Z1. As indicated previously, dc current flow in living tissue is, for most applications, highly undesirable because it promotes tissue growth or tissue destruction. The coupling capacitors of each output stage thus provide a simple and easy way to block any dc current flow through the output terminals "A" and "B", and hence through the tissue load Z1. (As is known in the art, a capacitor looks like an open circuit, i.e., an infinite impedance, to a dc current. Hence, a capacitor prevents or blocks dc current flow therethrough.)

Unfortunately, as mentioned above, the "simple and easy" dc blocking capacitors C1 and C2 do not come without a cost. In order for the coupling capacitors to readily pass ac current pulses of sufficient magnitude (so that an appropriate stimulation current may be applied to the electrodes 22 and 24), it is necessary that the coupling capacitors be of moderate value, e.g., on the order of 0.1 μfd. The "cost" in this instance is thus the relatively large size of such capacitors, particularly when sixteen such capacitors are required.

Figure 2A:
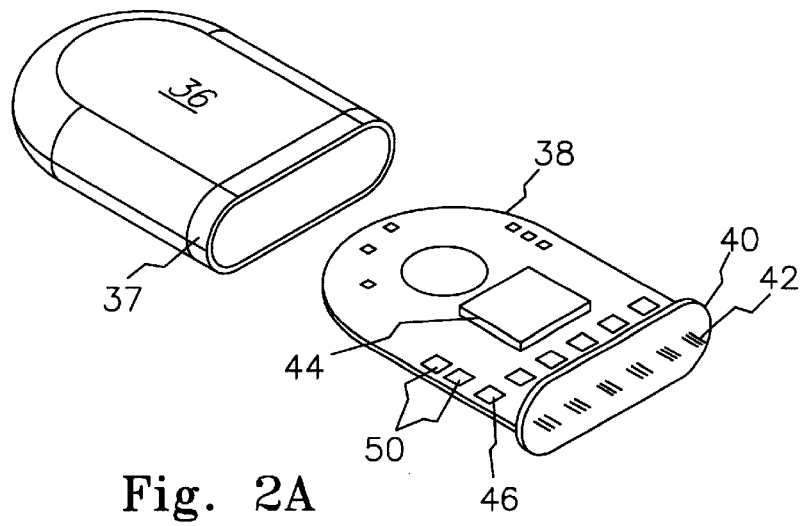
FIG. 2A shows an exploded view of an eight channel cochlear stimulator of the prior art, and illustrates the relative size, placement and volume of eight of the sixteen coupling capacitors that are used, two for each channel, in order to prevent dc current from flowing through the electrodes.
Figure 2C:
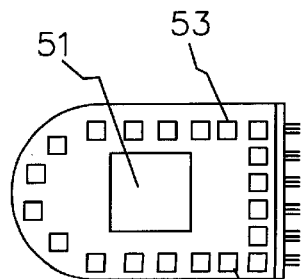
FIG. 2C depicts another design of a multichannel stimulator and shows the relative area used by the coupling capacitors compared with the chip.
Figure 2B:
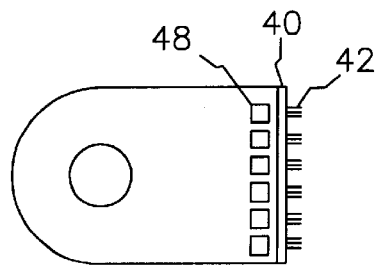
FIG. 2B illustrates the other side of the circuit board shown in FIG. 2A, and shows the placement and relative size of the other eight coupling capacitors that are used within the device.

To illustrate the "cost" of using coupling capacitors, reference is made to FIGS. 2A, 2B and 2C. FIGS. 2A and 2B graphically depict an exploded sketch of an existing 8-channel implantable cochlear stimulator (ICS) manufactured by Advanced Bionics Corporation of Sylmar, Calif. The electronic circuitry used in such device is described in the above-cited patent application. (It is to be noted that an electrode array and corresponding lead that attaches the electrode array to the ICS of FIG. 2 are not shown in FIG. 2.)

As seen in FIG. 2, the ICS includes a ceramic case 36 into which a circuit board 38 is inserted. The circuit board 38 includes a header 40 at one end thereof which, after the circuit board is inserted into the case 36, is hermetically sealed to a ring 37, which ring in turn is hermetically bonded to the case 36 using a process that is described generally in U.S. Pat. No. 4,991,582. Feedthrough terminals 42 provide the "A" and "B" output terminals for connecting to the electrodes through a suitable lead (not shown).

The ICS depicted in FIGS. 2A and 2B has approximate dimensions of 2.5 by 1.0 by 0.6 cm. A chip 44 is mounted on the board 38. The chip is made using 5 micron technology (where 5 microns relates to the nominal line widths and line spacing on the chip, and where one micron is equal to one millionth of a meter). The "footprint" size of the chip is about 0.42 by 0.38 inches, which is equal to approximately 0.16 square inches. Most all of the electronic circuitry associated with the ICS resides on the chip 44. only a few larger discrete components, such as a first row of coupling capacitors 46 on one side of the board (FIG. 2A), and a second row of coupling capacitors 48 located on the other side of the board (FIG. 2B), and power supply storage capacitors 50, are used within the ICS, but are not included as part of the circuitry on the chip 44.

Significantly, the rows of coupling capacitors 46 and 50 occupy a substantial portion of the space on the circuit board 38 and volume within the ICS case 36. More particularly, the sixteen 0.1 μfd coupling capacitors have a combined "footprint" of about 0.2 square inches, which is significantly greater than the footprint of the chip. Note that in other stimulators, e.g., FES mode stimulators, high current and large pulse widths are required that mandate capacitors on the order to 1, 5 and/or 10 μfd be used. Hence, the "footprint" of such capacitors is significantly greater than the footprint of the chip.

As the CMOS technology used on the chip 44 advances, e.g., to a 0.5 to 1 micron size or smaller, the space and volume occupied by the coupling capacitors becomes even greater. This is illustrated in FIG. 2C which shows a modern multichannel stimulator realized using a chip 51 designed using 0.8 micron technology. Such chip 51 has approximate dimensions of 0.25×0.25 inches, providing a footprint of roughly 0.0625 square inches. The sixteen coupling capacitors 53 used with the chip 51 have a combined footprint of about 0.20 square inches, almost four times larger than the chip itself! It is thus seen that an ICS, or other living tissue stimulator that could eliminate the coupling capacitors, even at the expense of additional circuitry on the chip 44 or 51, would clearly represent an advance in the art because the overall size of the stimulator device could be significantly reduced.

Figure 3:
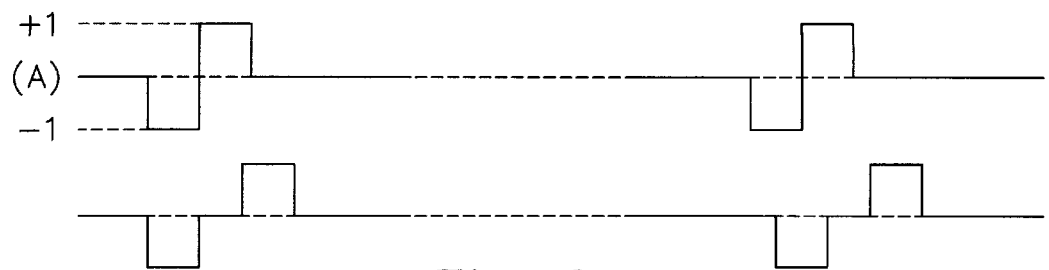
FIG. 3 depicts two types of biphasic stimulation current pulses that have commonly been used in the art.

Turning next to FIG. 3, there is shown a waveform diagram that depicts the common types of biphasic stimulation current pulses that are most commonly used by implantable living tissue stimulators. Each biphasic current pulse includes a pulse of one polarity (usually the first pulse is negative) followed immediately (or within a very short time) by an equal pulse of opposite polarity. When such biphasic current pulses are fed through a coupling capacitor, the positive current flow through the capacitor (and hence to the living tissue) is always equal to the negative current flow, and hence no dc component exists within the stimulating current. However, if no coupling capacitors are used, even if extreme care is exercised in trying to initially generate the positive portion of the biphasic pulse so that it is always equal to the negative portion, there is likely to be some amount of offset or imbalance that, over time, will produce an average dc current flow that may cause undesirable effects on the tissue.

Figure 4:
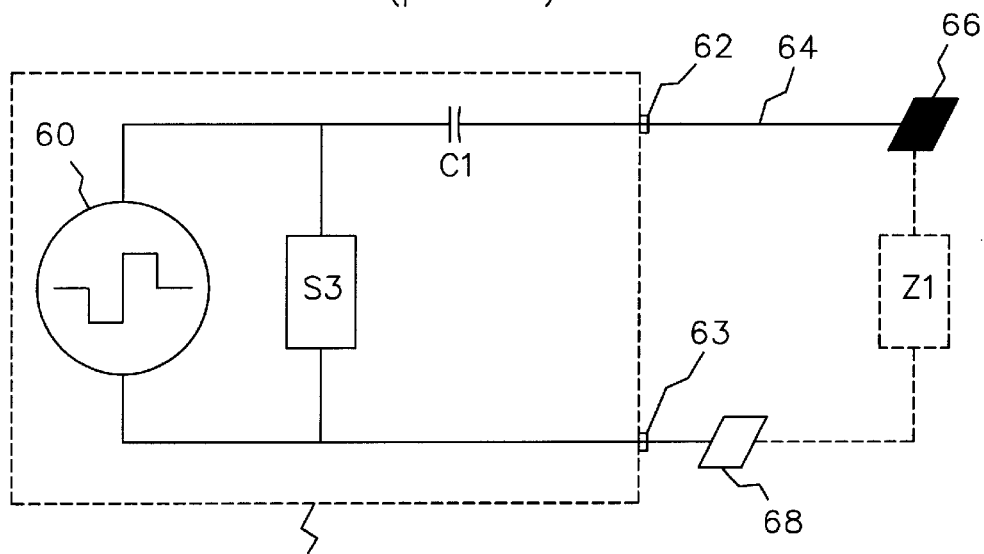
FIG. 4 is an equivalent circuit of the output stage of a single monopolar channel of a tissue stimulator of the prior art.

To avoid the potentially damaging dc current flow in the tissue being stimulated, it has heretofore been the practice of most prior art devices to employ coupling capacitors at the output stage so as to prevent dc current flow in the living tissue, as shown in FIG. 4. FIG. 4 illustrates a single output stage of a typical implantable stimulator 58 of the prior art configured for operation in a monopolar mode. In such an output stage, a biphasic current generator 60 supplies its biphasic stimulation pulse to an output terminal 62 through a coupling capacitor C1. The output terminal 62, in turn, is connected through a suitable lead conductor 64 to an electrode 66 that has been positioned within the living tissue at a desired stimulation location. For monopolar stimulation, a reference electrode 68 provides a return path for the biphasic stimulation current that is applied to the stimulating electrode 66. In order to prevent build up of charge on the capacitor C1, a switch S3 may be employed to short the capacitor C1 between biphasic pulses, as described above. The living tissue being stimulated, represented in FIG. 4 as element "Z1", thus represents the electrical "load" through which the biphasic stimulus flows.

It is noted that while a single monopolar stimulation channel is shown in FIG. 4, the same approach of using coupling capacitors to block the flow of dc current through the living tissue load is used for bipolar stimulation channels. For the description of the invention that follows, reference will be made to a single channel output stage that stimulates in a monopolar mode, as shown in FIG. 4. It is to be understood, however, that the invention may also be used with bipolar stimulation or multipolar stimulation. In a bipolar or multipolar channel, two electrodes are placed near the stimulation location, and coupling capacitors are used to interface with each output terminal and/or electrode, as shown in FIG. 1. As long as there is at least one bipolar capacitor in series with the tissue, the tissue is protected from dc current. (A "bipolar" capacitor is one that can have any polarity applied thereto and still function as a capacitor.)

Figure 5:
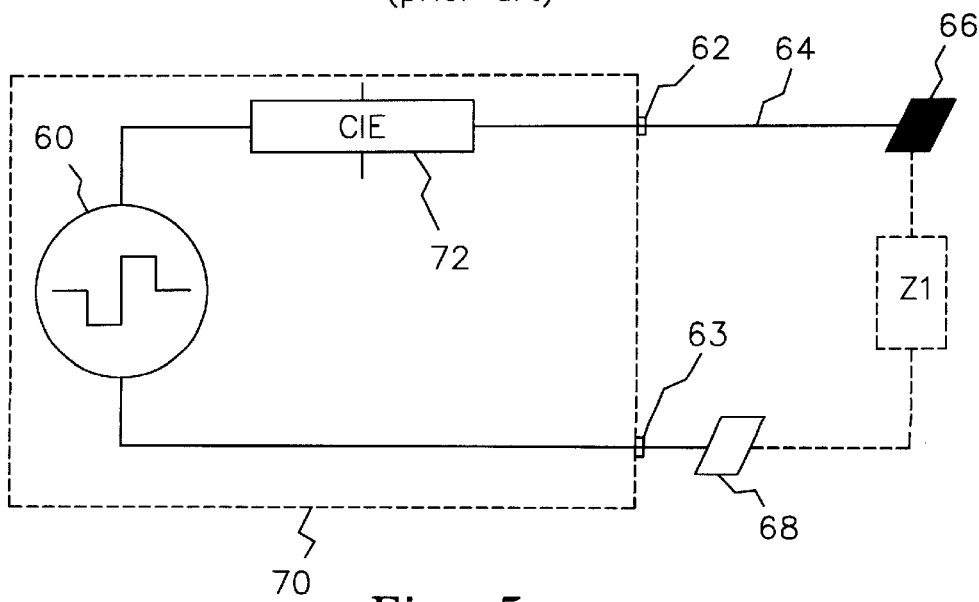
FIG. 5 is an equivalent circuit of the output stage of a single monopolar channel of a tissue stimulator, and shows the use of a replacement circuit within the implanted stimulator that replaces the coupling capacitor.

The present invention advantageously provides an implantable stimulator that allows biphasic stimulation pulses to be applied to living tissue without using large and bulky coupling capacitors, and yet still prevents average dc current flow from flowing through the tissue. The basic concept of the present invention is illustrated in the block diagram of FIG. 5. It is seen that FIG. 5 is the same as FIG. 4 except that the output coupling capacitor C1 of FIG. 4 has been replaced in FIG. 5 with a circuit 72, which circuit 72 functions as the "equivalent" of the capacitor C1 (and is thus also referred to as the capacitor C1 equivalent, or C1E). The circuit 72, or C1E, thus performs the same basic function as does a coupling capacitor, i.e., it prevents average dc current from flowing through the living tissue Z1.

Hence, in a broad characterization, the present invention may be described as an implantable living tissue stimulator that includes: (1) a sealed case 70 (usually an hermetically sealed case) having a plurality of feed-through terminals 62 and 63; (2) first circuit means (the biphasic current source 60) inside of the sealed case for generating a stimulating current pulse; and (3) second circuit means (the circuit 72) within the sealed case for providing an electrical current path between the first circuit means and a selected pair of the plurality of feedthrough terminals through which the stimulating current pulse may pass (which, for the simplified single channel of FIG. 3 comprises the pair of feedthrough terminals 62 and 63, but which for multichannel stimulators could comprise any pair of feedthrough terminals associated with any channel), and for blocking dc current flow through the electrical current path.

Advantageously, as described below, the second circuit means 72, i.e., the equivalent-to-the-capacitor-C1 circuit C1E, comprises a plurality of circuit elements that does not include a separate discrete coupling capacitor in the electrical current path. (It should be noted that very small capacitors, on the order of 0.000010 μfd [10 pf] may be used on the integrated circuit chip without taking up any significant footprint space. The thickness of such very small capacitors is less than 0.001 inches.)

One embodiment of the circuit C1E of FIG. 5 comprises digital signal processing (DSP) circuitry and/or analog circuitry that simulates a coupling capacitor of a specified size, e.g., 0.1 μfd. It is known that the current flow through a capacitor is defined as:

$$i = C(dv/dt) \quad (1)$$

where i is the current that flows in and through the capacitance, C is the capacitance, and v is the voltage across the capacitance. Hence, in accordance with this embodiment, DSP and/or analog circuitry is utilized to control the current that flows through the circuit C1E so that it is defined by Eq. (1). Note that the term dv/dt in Eq. (1) goes to zero for large values of dt (i.e., for long time periods, or dc), except when the biphasic current pulse is applied by the generator 60. As a result, the biphasic current pulse is allowed to pass through the circuit C1E, but dc current is not.

Those of skill in the art can readily fashion DSP and/or analog circuitry that will control the current through the circuit 72 in accordance with Eq. (1) above. While such DSP circuitry may utilize a significant number of CMOS transistors, configured into appropriate processing and logic circuitry, the overall space required by such DSP or other circuitry on the chip 44 (FIG. 1), or a supplemental chip, particularly given the smaller trace sizes associated with modern CMOS devices (0.8 micron and smaller) could still be less than using discrete coupling capacitors.

It should also be noted that the purposes of the present invention can be achieved without having the circuit 72 function exactly like the capacitor C1. That is, all the circuit 72 need do is to allow biphasic pulses or alternating current signals to pass through it without allowing any dc components. Such function can be achieved by adjusting the second pulse of a biphasic pulse pair, in amplitude and/or width, to precisely cancel out any dc component resulting from the first pulse of the biphasic pulse pair. Likewise, the amplitude of the positive or negative components of an ac signal can be increased or decreased independently to prevent any dc components.

Figure 6:
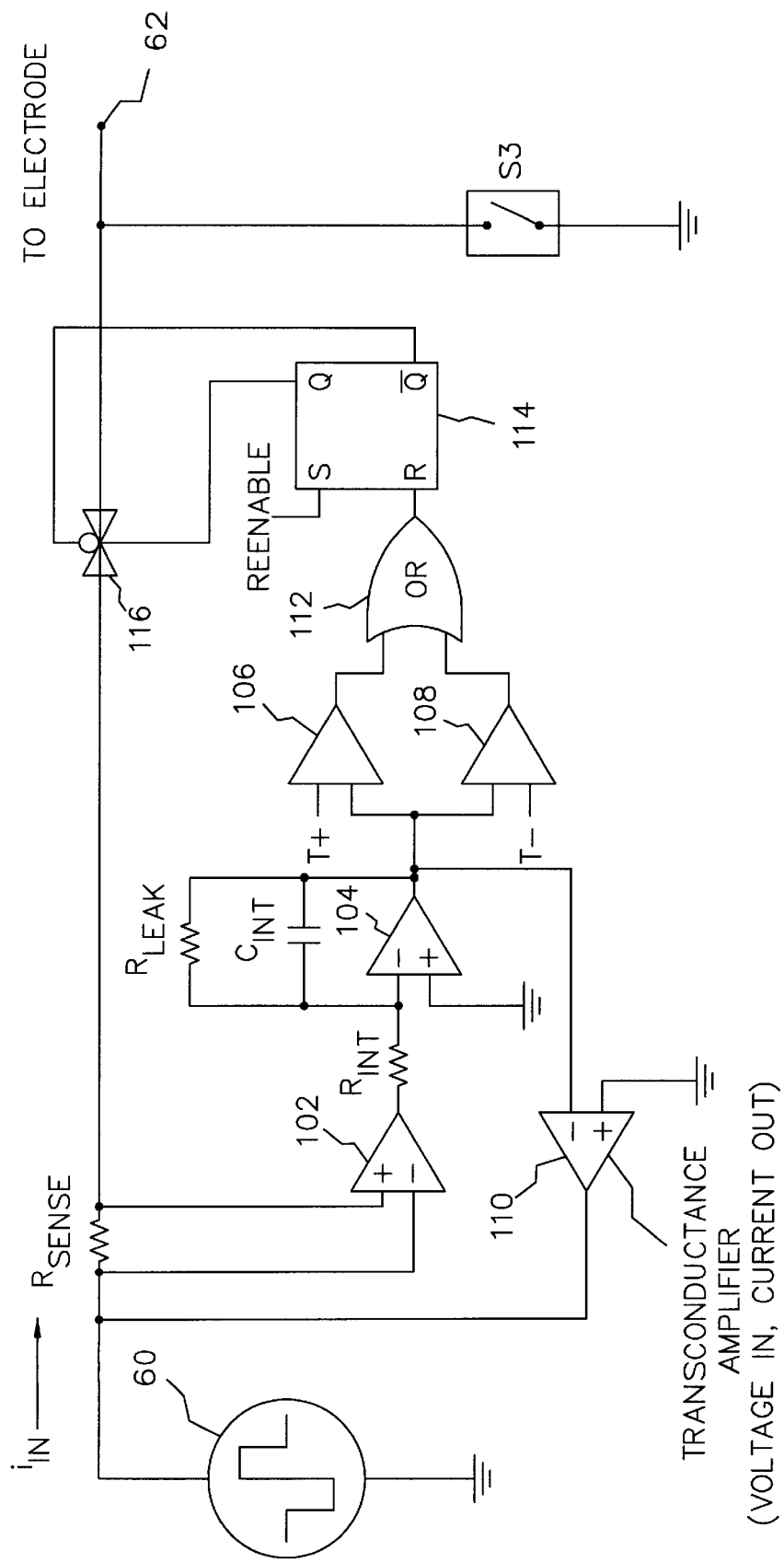
FIG. 6 is an electrical schematic diagram of a first embodiment of the replacement circuit of FIG. 5, which circuit includes a current-sense resistor to monitor the electrical current flowing therethrough.

One embodiment of the C1E circuit 72 in FIG. 5 is shown in FIG. 6. The circuitry of FIG. 6 limits the average dc current provided to the output terminal 62 (and hence to the electrode 66; FIG. 5). It accomplishes this function in two ways: (1) it cuts off, or blocks, the dc current applied to the output terminal when it exceeds a prescribed threshold; and (2) it balances (adjusts) the charge delivered to the output terminal 66 through a biphasic stimulation pulse, thereby preventing any net dc current flow between the output terminals.

The electrode current $i_{in}$ is sensed by the resistor $R_{SENSE}$. The value of $R_{SENSE}$ is chosen to give maximum voltage drop (at the highest stimulus current $i_{in}$) that will not seriously limit operation. The voltage drop across $R_{SENSE}$ (which is directly proportional to the current $i_{in}$) is amplified and referenced to ground potential by a differential amplifier 102. This amplified signal is then integrated by a "leaky" integrator circuit comprised of operational amplifier 104, resistor $R_{INT}$, capacitor $C_{INT}$ and resistor $R_{LEAK}$.

The time constants of the "leaky" integrator circuit are chosen to be much longer than the typical pulses associated with a biphasic stimulation pulse. The result is that the circuit only responds to average dc current.

The output signal from the integrator is applied to two comparator circuits 106 and 108, which respectively compare such integrated output signal to two preset levels T+ and T−. If the integrator output is more positive than T+, or more negative than T−, the output of an OR gate 112 (connected to receive as input signals the respective output signals of the comparator circuits 106 and 108) is asserted. This assertion causes set/reset latch 114 to be reset. Resetting latch 114, in turn, causes a transconductance switch 116, placed in series with the output terminal 62, to be switched off, thereby disconnecting the output. The output remains disconnected until a "reenable" signal is applied to the set terminal of the latch 114. Such reenable signal is asserted, e.g., when power is first applied to the stimulator, or upon command from an external controller (programmer).

The sensitivity of the dc current cut-off portion of the circuit of FIG. 6 is determined by the values of $R_{SENSE}$, $R_{INT}$, $R_{LEAK}$, the gain of the Differential Amplifier 102, and the values of T+ and T−. By way of example, the sensitivity of a cochlear stimulator may be set to a value that causes the output terminals to be disconnected whenever an average error (dc current) of, e.g., 1 μa occurs.

The charge balancing portion of the circuit of FIG. 6 utilizes the sense resistor $R_{SENSE}$, differential amplifier 102, and integrator circuit 104 (and associated $R_{INT}$, $R_{LEAK}$ and $C_{INT}$) as described above. The output of the integrator is applied to a transconductance amplifier 110. A transconductance amplifier 110 provides a current output that is proportional to the voltage input. The current output from the transconductance amplifier 110 is injected back into the main current path, which current tends to cancel any net dc current.

The dc loop gain of the cancellation portion of the circuit of FIG. 6 is set by the values of $R_{SENSE}$, $R_{INT}$, $R_{LEAK}$, and the gains of the differential amplifier 102 and the transconductance amplifier 110. By way of example, for a typical cochlear stimulator, the dc loop gain may be set so that an average error of 1 μa results in a correction current of 10 μa. Such a loop gain thus causes an average dc error in the original stimulus current to be reduced by a factor of 10.

Figure 7:
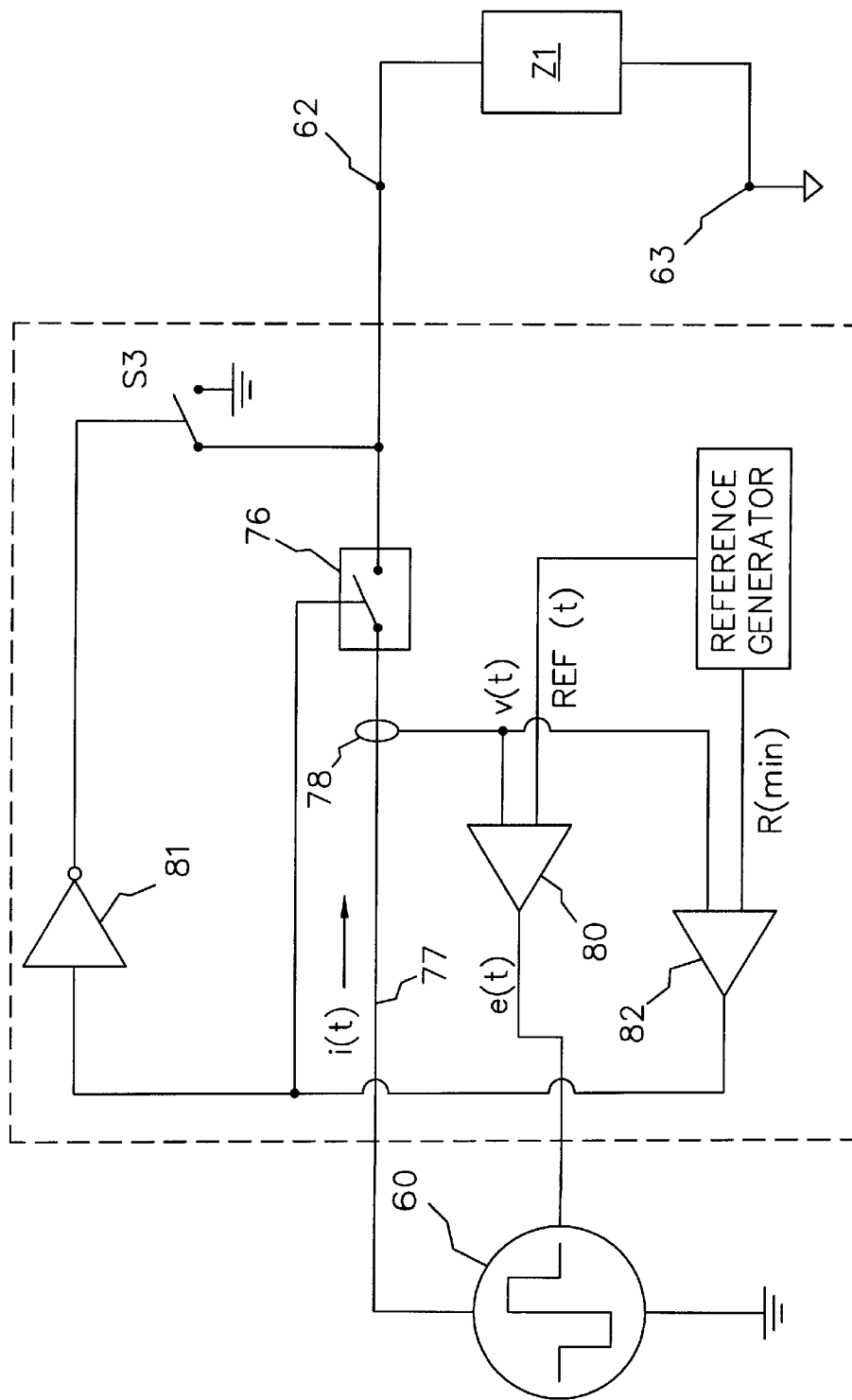
FIG. 7 is a functional block diagram of a second embodiment of the replacement circuit of FIG. 5, which replacement circuit includes a current probe to monitor the electrical current flowing therethrough.

Turning next to FIG. 7, a functional block diagram is shown of another embodiment of the C1E circuit 72 of FIG. 5. In FIG. 7, a special circuit 74 monitors the current flow as a function of time, i(t), generated by the biphasic current pulse generator 60 and shuts-down such current flow, e.g., by opening a series switch 76, whenever the monitored current does not meet specified criteria. The specified criteria may be that the biphasic current pulse be truly biphasic, i.e., having a first current pulse followed by a second current pulse of equal but opposite polarity. The specified criteria may also require that the amplitude of any current pulse delivered to the output terminal be at least a prescribed minimum value or else the switch 76 is opened. Further, the specified criteria may similarly require that the amplitude of each pulse portion of a biphasic current pulse be less than a prescribed maximum value or else the switch 76 is opened.

As seen in FIG. 7, the circuitry 74 includes a current monitor or probe 78 that detects the current i(t) flowing from the biphasic current generator 60 to the output terminal 62 along a main current path 77. A switch 76 is in series with the current path 77. The current probe 78 generates an output voltage v(t) that varies as a function of the current i(t). Such output voltage v(t) is compared with a reference signal, Ref(t), in a first comparator circuit 80. The reference signal, Ref(t) is generated by a reference generator circuit 84. The reference signal, Ref(t), may take the form, e.g., of the biphasic current waveforms depicted in FIG. 3. The first comparator circuit 80 generates an output error signal e(t) whenever the monitored current i(t), as represented by the voltage v(t), does not match the reference criteria Ref(t). Such error signal e(t) is then fed back to the biphasic current generator 60, where it is used to control the formation of the biphasic current pulse i(t) so that the error signal e(t) is driven to zero. In this manner, using negative feedback, the biphasic current generator 60 is forced to generate a biphasic stimulation current i(t) that faithfully follows the reference signal Ref(t). Hence, by defining the reference signal Ref(t) to be a true biphasic signal, which means no average dc current is present, dc current flow in the living tissue is avoided.

The current monitoring circuit 78 also preferably includes a second comparator circuit 82 that compares the output voltage signal v(t) to a minimum reference level R(min). Whenever the output voltage signal v(t), which is proportional to the current i(t), drops below the minimum reference level R(min), the switch 76 is opened, and the output terminal 62 is shorted to ground through the switch S3. Hence, the second comparator circuit 82 provides a fail-safe step to assure that small currents, e.g., currents below a defined threshold, are not allowed to flow through the living tissue. The output of the second comparator circuit 82 further drives an inverter gate 81, or equivalent drive circuit, that controls the switch S3 so that whenever the switch 76 is opened, the output terminal 62 is shorted to ground. A third comparator circuit (not shown in FIG. 7) could likewise be used to compare v(t) to a maximum reference level R(max), and thereby also open the switch 76 (and short the output terminal 62) to assure that large currents, e.g., currents that might be painful or harmful to the patient, are not allowed to flow through the living tissue. Thus it is seen that when switch 76 is opened, inverter 81 causes shorting switch S3 to close, thereby discharging the capacitance associated with the output terminals 62 and 63 (and any electrodes connected thereto) in the event a slight charge imbalance causes a charge to remain.

The comparator circuits 80 and 82 (and others, if used), as well as the reference generator circuit 84, and the inverter 81, may be of conventional design, with a very low quiescent supply current requirement.

The current probe 78 may likewise be of conventional design. Any circuit that faithfully generates an output voltage v(t) that is proportional to the current flow i(t) may be used as the current probe. A current sense resistor, $R_{SENSE}$, coupled to a differential amplifier to measure the voltage across the resistor, $R_{SENSE}$, such as is shown in FIG. 6 above, may thus be used as the current probe.

Further, the function of current probe 78 may be realized using a coulomb counter that generates a coulomb-indicating voltage $v_i$ that varies as a function of the integrated coulomb count flowing in any one direction through the electrical current path. If necessary, two coulomb counters may be used, one for determining an integrated coulomb count for coulombs flowing in one direction through the current path, and another for determining another integrated coulomb count for coulombs flowing in the other direction in the current path.

Figure 8:
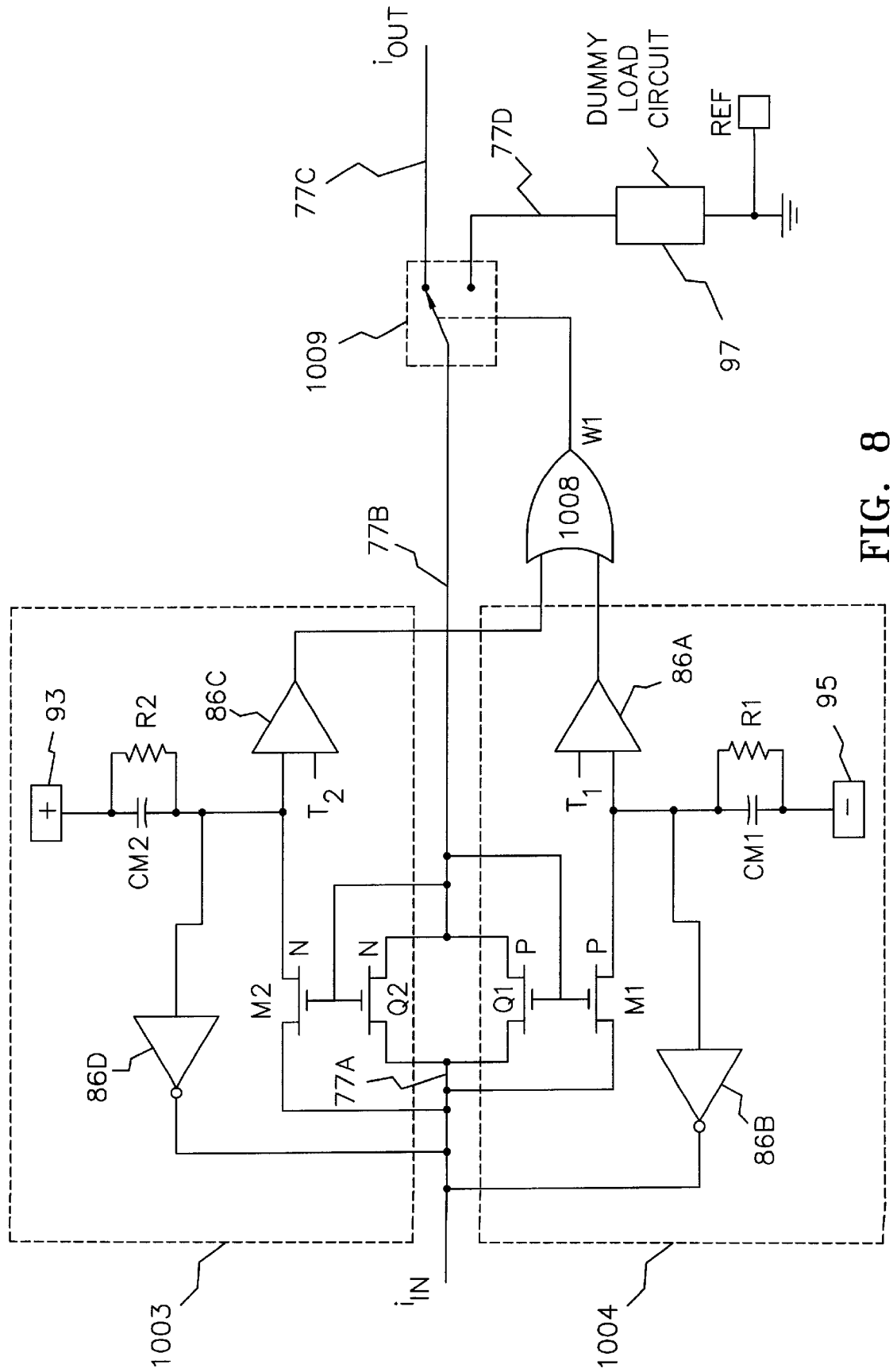
FIG. 8 is a functional schematic diagram of a pair of unidirectional current mirror circuits that may be used as the current probe within the replacement circuit of FIG. 7.

Another type of circuit that may be used as the current probe 78 are a pair of current mirror circuits. A suitable current mirror circuit is shown in FIG. 8. The circuit of FIG. 8 does not simulate a capacitor, but it does protect the patient from dc current flow. In FIG. 8, current mirror circuit 1004, comprising transistors Q1 and M1, samples a small amount of current flowing in one direction on line 77, and detects the average dc current by measuring the voltage $V_1$ that accumulates on the capacitor/resistor parallel circuit made up of capacitor CM1 and resistor R1. In a similar manner, current mirror circuit 1005, comprising transistors Q2 and M2, samples a small amount of current flowing in the other direction on line 77, and detects the average dc current by measuring the voltage $V_2$ that builds up on the capacitor/resistor parallel circuit made up of capacitor CM2 and resistor R2. Preferably, the transistors Q1 and M1 are realized from P-channel FETS (field effect transistors), while the transistors Q2 and M2 are realized using N-channel FETS.

In operation, the current mirror circuits function as follows: The transistors Q1 and M1 are P-channel CMOS (complementary metal oxide semiconductors) FETS, with the area of M1 being a small fraction of the area of Q1, e.g., 1/100th of the area of Q1. If current is flowing through the line 77, shown in FIG. 8 as being divided into three sections, 77A, 77B and 77C, in a direction such that the input terminal at $i_{in}$ is positive relative to the output terminal of $i_{out}$ (i.e., if section 77A is positive relative to section 77B), then 1/100th of the current flowing in 77A and through Q1 will flow through M1. This current through M1, in turn, charges up CM1 and flows through R1 to the negative rail terminal 95. The values of CM1 and R1 are selected to provide a voltage V that is a running average of the dc current flowing through R1 and charging up CM1.

If the current flowing through 77A, 77B and 77C is reversed, i.e., if the current is in a direction such that the input terminal $i_{in}$ is negative relative to the output terminal $i_{out}$ (that is, if section 77A is negative relative to section 77B), then the N-channel FETS Q2 and M2 function in a manner similar to that described above for Q1 and M1 as the current mirror for the current flowing in that direction.

As indicated previously, Q1 and M1 are P-channel FETS. As seen in FIG. 8, the gate of Q1 is tied to the drain of Q1, and M1 has its source and gate tied to the source and gate of Q1 respectively. The drain of M1 is tied to a negative point when a current is flowing through Q1 such that its drain is negative relative to its source (i.e., such that line 77B is negative relative to line 77A). Under such conditions, the current flowing through M1 will be a fraction of the current flowing through Q1, where such fraction is equal to the fraction of the area of M1 compared to the area of Q1.

As also indicated previously, Q2 and M2 are N-channel FETS. As further seen in FIG. 8, the gate of Q2 is tied to the drain of Q2, and M2 has its source and gate tied to the source and gate of Q2 respectively. The drain of M2 is tied to a positive point when a current is flowing through Q2 such that its drain is positive relative to its source (i.e., such that line 77B is positive relative to line 77A). Under such conditions, the current flowing through M2 will be a fraction of the current flowing through Q2, where such fraction is equal to the fraction of the area of M2 compared to the area of Q2, and where this area relationship is the same as the area relationship of Q1 and M1.

The voltages $V_1$ and $V_2$ represent the average dc current flowing in each of the two directions. Such voltages are buffered and amplified by high gain comparator circuits 86A and 86C, respectively, whenever they exceed reference threshold values $T_1$ and $T_2$, respectively. The values of $T_1$ and $T_2$ are set so that the comparator output is a digital "1" whenever an average dc current (as represented by the voltages $V_1$ or $V_2$) is present on line 77B, regardless of its direction or polarity, that is greater than a specified value. Whenever such dc current is detected, as manifest by the digital "1" at the output of comparator 86A and/or 86C, a digital "1" will also appear at the output of exclusive OR gate 1008. The output of exclusive OR gate 1008 may be viewed as a control signal $W_1$ that controls electronic switch 1009. If $W_1$ is a digital "1", for example, electronic switch 1009 is switched so that such dc current is directed from the $i_{out}$ terminal (77C) to a dummy load circuit 97. If $W_1$ is a digital "0", then electronic switch 1009 allows the current to flow to/from the $i_{out}$ terminal.

In addition, whenever any average dc current is present, as manifest by the presence of the voltages $V_1$ and/or $V_2$, inverter amplifiers 86B and 86D partially amplify and invert the dc voltage and feed a small current back to line 77A. This action reduces the average dc current flowing to/from the $i_{out}$ terminal and section 77C whenever the average dc current remains below the threshold reference values $T_1$ and $T_2$. In this manner, it is seen that the circuit of FIG. 8 functions as a current probe for which an output voltage $v_i$ ($V_1$ and/or $V_2$) is generated representative of the average input current, and a control signal $W_1$ is generated indicating whether acceptable ("0") or unacceptable ("1") levels of average dc current are present.

Figure 9:
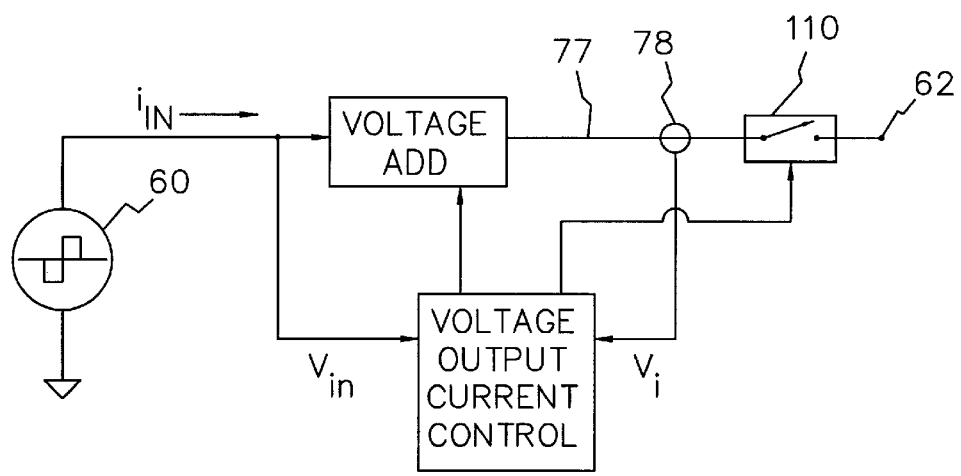
FIG. 9 is a functional block diagram of a third embodiment of the replacement circuit of FIG. 5.

Turning next to FIG. 9, yet another embodiment of the C1E circuit 72 of FIG. 5 is illustrated. The circuit shown in FIG. 9 represents a simplified version of a simulated capacitor. It prevents average dc current flow from being applied to the output terminal 62 in much the same manner as is described above in connection with either FIG. 6 and/or FIGS. 7 and 8. That is, a current probe 78, or equivalent current monitoring circuit, measures the current flow through the main current path 77. When such monitored current exceeds a prescribed threshold(s), an in-line switch 110 is activated to disrupt the current path, e.g., open the current path, or direct the current path to an equivalent load, thereby blocking such current from being applied to the output terminal. The circuit of FIG. 9 further includes a voltage add circuit 114 that selectively applies a voltage level between the source 60 and the output terminal 62 in the same manner that a voltage would build up on a coupling capacitor if such coupling capacitor were inserted between the source 60 and the output terminal 62. To this end, a voltage control circuit 112 monitors the amplitude of the current pulses provided by the source 60 through a current probe 78, or equivalent device. The control circuit 112 also monitors the voltage, $v_{in}$, associated with such current pulses as provided by the source 60. Knowing the current and voltage associated with the source pulses, the control circuit 112 is then able to generate an appropriate voltage that is inserted in-line with the current path 77, e.g., much as if a small battery were inserted in series in the current path. Such inserted voltage may be achieved by appropriate biasing of FET transistors and/or diodes and/or other semiconductor-junction devices as is known in the art.

Figure 10:
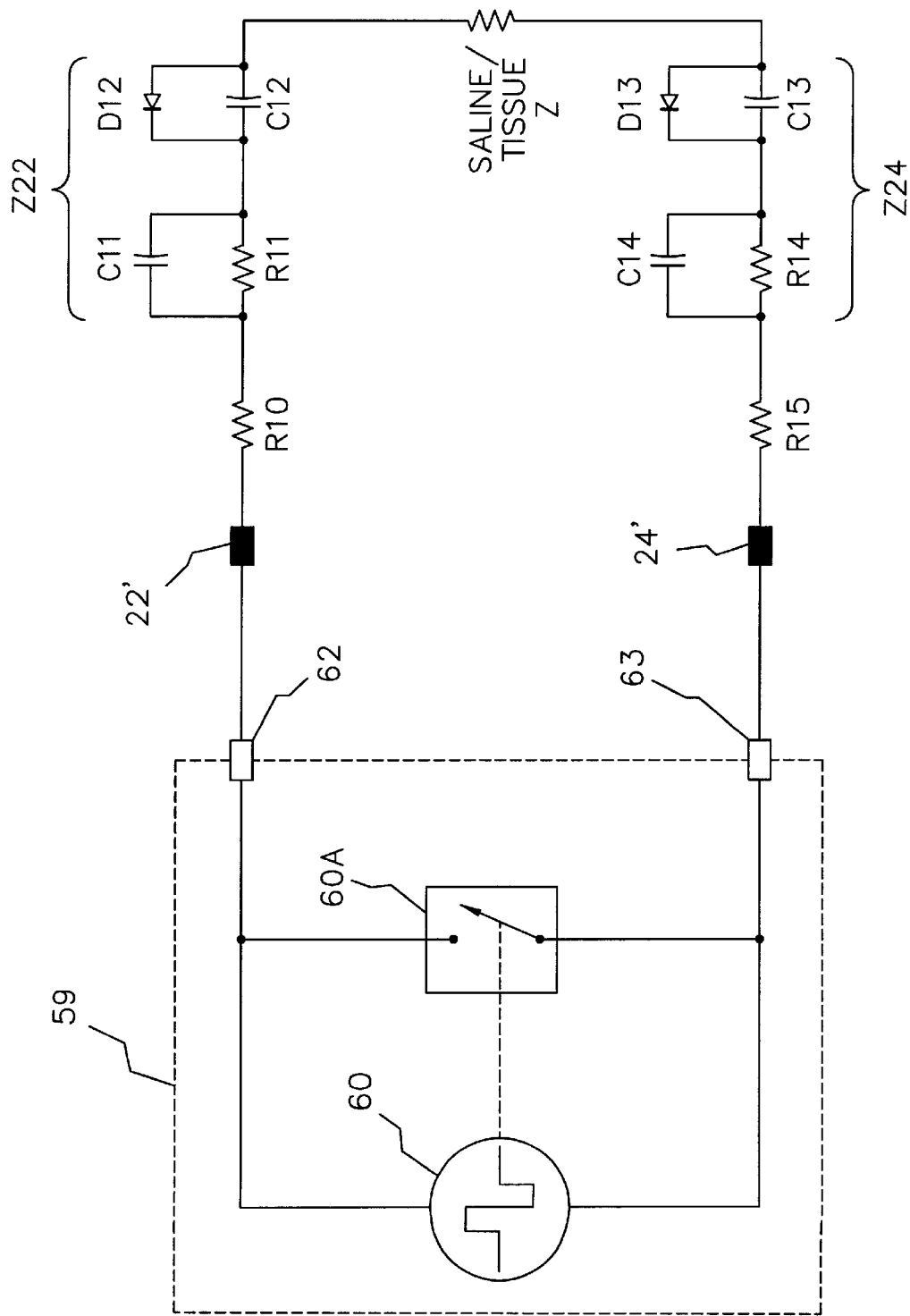
FIG. 10 shows a further embodiment of the invention wherein the output coupling capacitors are moved from inside of the implanted device to the electrodes.

Turning next to FIG. 10, another alternative embodiment of the invention is schematically depicted. In FIG. 10, there is no "C1E" circuit 72 utilized in the output stage 59 of the implantable stimulator, as is done for the embodiments described above in connection with FIGS. 5–9. Rather, in FIG. 10, the coupling capacitor, or the equivalent of the coupling capacitor, is moved from inside the implanted stimulator 59 to the electrodes 22' and 24'. As illustrated in FIG. 10, the coupling capacitor is actually formed by using the electrode-saline interface that results when a conductive electrode comes in contact with saline body fluids. In FIG. 10, Z22 represents an approximate model of the complex impedance between electrode 22 and the saline in the tissue (saline impedance). Likewise, Z24 represents the complex impedance between electrode 24 and the saline. Capacitor C12 and diode D12 (as well as capacitor C13 and diode D13) represent the passivation or oxide insulation layer that exists at the surface of each stimulating electrode.

The most common electrode materials used for tissue stimulation electrodes are platinum or the alloy platinum (90%)-iridium(10%). Other metals have been used that do not corrode when subjected to the stimulating currents. In all cases for these electrode materials, there is a passivation or oxide insulting layer that forms a capacitor with the saline for one polarity of stimulation current. This oxide insulting layer has a breakdown voltage on the order of 1 or 2 volts. Interestingly, with the opposite polarity current, the oxide acts as a forward biased diode. Since there are always two electrodes, there is thus at least one capacitor in series with the stimulator.

Another way of looking at this phenomena is through the circuit model shown in FIG. 10. As seen in FIG. 10, since the diodes (D12 or D13) are pointing in opposite directions, one is always back biased and the capacitor (C12 or C13) in parallel with that diode is thus available to function as a capacitor. The capacitor in parallel with the forward biased diode is shorted, and is thus not available to function as a capacitor.

The difficulty with the functional capacitor as far a dc protection is concerned is the low breakdown voltage. To deal with such low break down voltage, the invention places a switch (60A) across the two electrodes to discharge the electrode-saline interface capacitance after each stimuli. Thus, if there is a small mismatch between the positive and negative phases of each biphasic stimuli, the small build up of charge on the capacitance from the phase with the larger amplitude will be discharged through the switch (60A) and will never get a chance to build up to a value that could cause breakdown to occur. If the charge were to build up past the voltage break down point, dc current would flow through the tissue.

The scheme shown in FIG. 10 works fine with low frequency stimuli (i.e., with low frequency trains of stimulus pulses). However, with high frequency stimuli (in excess of 1000 stimuli per second), there is insufficient time for the shorting switch (60A) to discharge the charged up capacitance (C12 or C13). This is because of the series resistance resulting from the interface impedance and the saline/tissue impedance (R10, R11, Saline/Tissue Z, R14 and R15). The result is that with a configuration as shown in FIG. 10, and with high frequency stimulation, the voltage can build up on the interface capacitance (C12 or C13) and cause a voltage breakdown that can permit dc current to flow through the tissue.

One of the stimulation strategies presently used for cochlear stimulation is continuous interleaved sampling (CIS). CIS strategy requires stimulus frequencies in excess of one thousand stimuli per second. Also, for other applications, stimuli frequencies in excess of 1000 stimuli per second are commonly used, e.g., to block or artificially fatigue neurons or muscle fibers.

Advantageously, the present invention solves the above problem (of high frequency stimuli) in a unique way. An additional requirement for many electrode situations (such as a cochlear stimulating electrode) is that the electrode be very small. For example, for a cochlear electrode, the electrode may be on the order of 0.02 by 0.02 inches, and very thin, i.e., not protrude above the surface of the insulating cable. Normally the electrode is flush with the insulating cable. There exists a certain class of subminiature capacitors that are made by using the anodized surface of an open cell of sintered powder metal of an anodizable material. The breakdown voltages for these classes of metals can be made quite high, e.g., on the order of 10 to 20 volts or higher. Among the metals that can be anodized to higher voltages are titanium, niobium, tantalum, and columbium. For example, tantalum capacitors are made using this principal. Eighteen angstroms of tantalum oxide has a voltage breakdown of about one volt. Normally, a 3.5 to 4 times safety factor in breakdown voltage is required. Hence, by anodizing tantalum to produce a tantalum oxide layer that exhibits a breakdown voltage of 80 volts, a very reliable capacitor is realized having a specified breakdown voltage of 20 volts. Usually, such tantalum capacitors have a special conductor (which can be solid or liquid) and which makes contact with the anodized layer and which forms the other plate of the capacitor. By using a fine sintered powder, a very large surface area is possible, leading to a high capacitance capacitor.

It is known in the art, see, e.g., U.S. Pat. No. 5,193,540 (Schulman et al.) and Guyton and Hambrecht, "Theory and Design of Capacitor Electrodes for Chronic Stimulation", *Med. Biol. Engr.* Vol. 12, pp. 613–619 (1974), that a material such as open cell sintered tantalum can function quite well as both an electrode and an electrolytic storage capacitor, with the saline of the living tissue being the plate in contact with the non-metallic side of the oxide layer. Recently, very fine tantalum oxide powder has become available. The present invention recognizes that such fine tantalum oxide powder may be used to create high value capacitances due to the exposed very large surface area. Using such a material, it is now possible to attach a 0.001 to 0.002 inch thick layer of sintered tantalum over each platinum electrode. A 0.02 by 0.020 by 0.002 inch layer of such high level sintered tantalum capacitor can result in capacitances on the order of 0.10 $\mu$fd having a breakdown voltage of about 15 volts. If the platinum electrode is receded about 0.002 inches, the electrode with the 0.002 inches of sintered tantalum will be flush with the outside surface. Also, if a large indifferent electrode is used it can be coated with a sintered open cell anodized material such as tantalum oxide and form a unipolarity capacitor. Mass production methods of coating the electrodes with the sintered metal are known.

One such method is plasma deposition. Another is sputtering the metal with oxygen present, and another is sputtering without oxygen present.

It is noted that sintered tantalum may be used as described above to coat the electrode, and thereby form a capacitor, even when the electrode is not made from platinum. All that is required is that the electrode metal be of a type that will not corrode in the pressence of body fluids, and that exhibits the desired mechanical properties of flexing and bending as are needed in an implantable electrode. For example, a metal that meets these requirements, and that can be used in lieu of platinum, is MP35 (a mutli-phase nickel alloy).

In coating the electrode with the sintered tantalum, it is important to assure that the tantalum properly adheres to the electrode metal. If the electrode metal is of a type to which tantalum does not readily adhere, then an intermediary metal, e.g., such as MP35, may be used.

Figure 11:
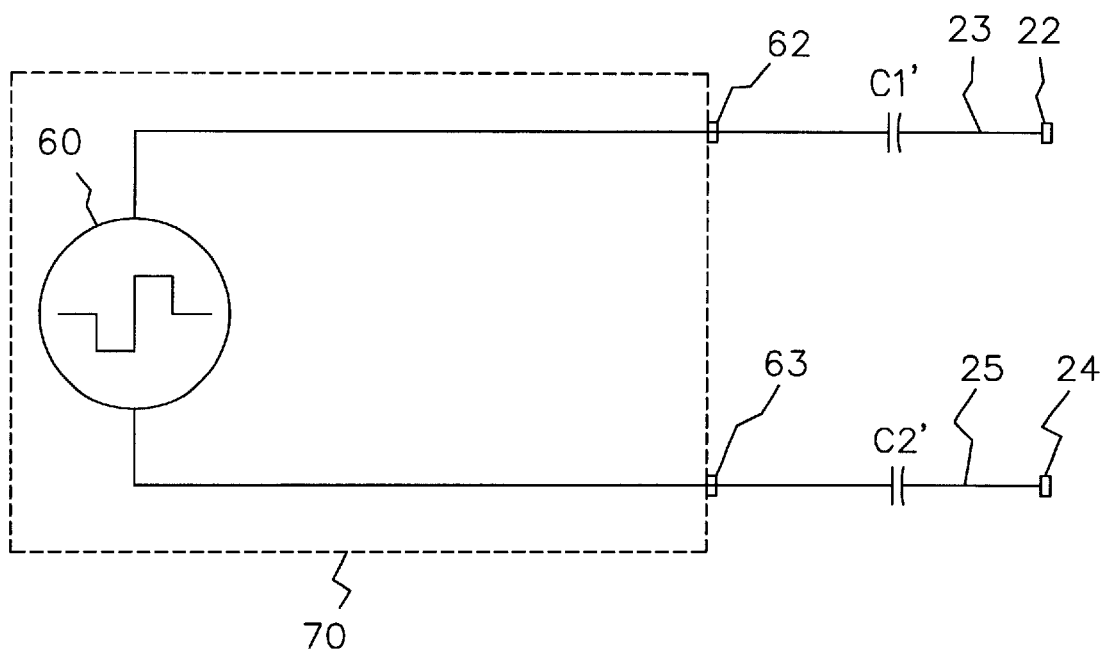
FIG. 11 shows yet another embodiment of the invention wherein the output coupling capacitors are moved from inside of the implanted device to the lead that connects the implanted device to the electrodes.

Referring next to FIG. 11, yet a further alternative embodiment of the invention is illustrated. In FIG. 11, a coupling capacitor C1 or C2 is integrated into the conductive lead 23 or 25 that connects the output terminal 62 or 63 with the electrodes 22 or 24.

Figure 12:
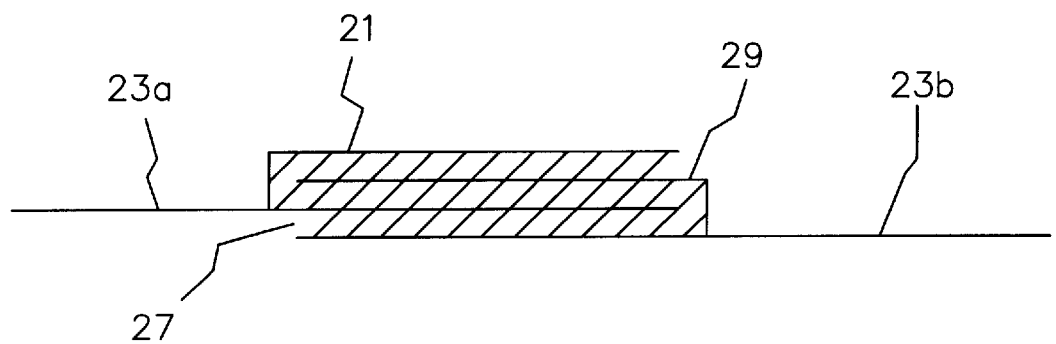
FIG. 12 shows a schematic cross-sectional view of a lead that includes a capacitor integrated as part of the lead in accordance with the embodiment of FIG. 11.

One way in which the capacitor C1' and/or C2' may be formed is by interleaving rolls of foil-like plates less than 0.001 inches thick between a suitable dielectric material as depicted in the cross sectional view of the conductor 23 (or 24) shown in FIG. 12. As seen in FIG. 12, a first conductor 23$a$ connects to a first plate 21, and a second conductor 23$b$ connects to a second plate 29. The first and second plates 21 and 29 are separated by a suitable insulating material 27, e.g., aluminum oxide, which insulating material is 0.0001 inches thick, and which functions as the dielectric material of the capacitor. The "plates" are then rolled together a specified number of turns, e.g., one to ten (or, for higher capacitance values, 10 to 100 turns) in order to achieve a desired capacitance value.

Other techniques may also be used to form the capacitors as an integral part of the leads 23 and 25. For example, a coaxial structure may be employed where one of the leads 23$a$ or 23$b$ is centered within a spiraling coil of the other, and wherein a suitable insulator separates the two leads.

Further, it is noted that an array of capacitors may be used, e.g., positioned just outside of the hermetically sealed housing, that are positioned to be in-line with the electrode/lead wires, thereby preventing dc current from flowing to the electrodes.

As described in the preceding figures and text, it is thus seen that the present invention provides an implantable living tissue stimulator that avoids the use of conventional coupling capacitors in its output stage, thereby significantly reducing the overall size and volume of the stimulator's output stage, yet still prevents any net dc current from flowing through the living tissue that is in contact with the electrodes of the stimulator.

While the invention herein disclosed has been described by means of specific embodiments and applications thereof, numerous modifications and variations could be made thereto by those skilled in the art without departing from the scope of the invention set forth in the claims.

What is claimed is:

1. An implantable living tissue stimulator comprising:
   a case having a plurality of feed-through terminals;
   first circuit means inside of the case for generating a stimulating current pulse; and
   second circuit means within the case for providing an electrical current path between the first circuit means and a selected pair of the plurality of feed-through terminals through which the stimulating current pulse must pass, and for blocking dc current flow through the electrical current path;

said second circuit means comprising a plurality of circuit elements that do not include a coupling capacitor and do not include a coupling transformer in the electrical current path.

2. The implantable living tissue stimulator of claim 1 wherein said case comprises a hermetically sealed enclosure.

3. The implantable stimulator of claim 1 wherein said second circuit means comprises electronic circuit simulating means for simulating a coupling capacitor placed in the electrical current path.

4. The implantable stimulator of claim 3 wherein said electronic circuit simulating means comprises:

current monitoring means for measuring the amount of current flowing through the electrical current path as a function of time;

voltage means for applying a controlled voltage potential to said electrical current path;

switch means for selectively opening and closing said electrical current path; and control means responsive to the current measured by the current monitoring means for selectively controlling the voltage means so that the controlled potential applied to said electrical current path varies as a function of how much voltage would build up on a coupling capacitor of a prescribed capacitance placed in said electrical current path, and for selectively controlling said switch means to open said electrical current path whenever the measured electrical current flowing in the electrical current path has not changed over a prescribed time period.

5. The implantable stimulator of claim 4 wherein said control means further includes means for controlling said switch means to open said electrical current path whenever the measured electrical current flowing in the electrical current path remains less than a prescribed current value.

6. The implantable stimulator of claim 4 further comprising a charge measuring means for measuring a coulomb value and wherein said control means further includes means for controlling said switch means to open said electrical current path whenever the measured electrical current flowing in the electrical current path remains less than a prescribed coulomb value.

7. The implantable stimulator of claim 4 wherein said first circuit means includes means for generating a biphasic current pulse comprising a first pulse of one polarity followed by a second pulse of the opposite polarity and wherein said control means further controls said switch means to open said electrical current path whenever one of the pulses of the biphasic current pulse is missing.

8. The implantable stimulator of claim 3 wherein said electronic circuit simulating means comprises:

current monitoring means for measuring the amount of current flowing through the electrical current path as a function of time;

voltage means for applying a controlled voltage potential to said electrical current path;

an equivalent load circuit;

switch means for selectively connecting said electrical current path to either the selected pair of the plurality of feed-through terminals or to said equivalent load circuit; and control means responsive to the current measured by the current monitoring means for selectively controlling the voltage means so that the controlled potential applied to said electrical current path varies as a function of how much voltage would build up on a coupling capacitor of a prescribed capacitance placed in said electrical current path, and for selectively controlling said switch means to connect said electrical current path to said equivalent load circuit whenever the measured electrical current flowing in the electrical current path has not changed over a prescribed time period.

9. The implantable stimulator of claim 8 wherein said control means further includes means for controlling said switch means to open said electrical current path whenever the measured electrical current flowing in the electrical current path remains less than a prescribed current value.

10. The implantable stimulator of claim 8 further comprising a charge measuring means for measuring a coulomb value and wherein said control means further includes means for controlling said switch means to open said electrical current path whenever the measured electrical current flowing in the electrical current path remains less than a prescribed coulomb value.

11. The implantable stimulator of claim 8 wherein said first circuit means includes means for generating a biphasic current pulse comprising a first pulse of one polarity followed by a second pulse of the opposite polarity and wherein said control means further controls said switch means to open said electrical current path whenever one of the pulses of the biphasic current pulse is missing.

12. The implantable stimulator of claim 8 wherein said current monitoring means comprises an integrating coulomb counter that generates a coulomb-indicating voltage $v_i$ that varies as a function of the integrated coulomb count flowing in any one direction through the electrical current path.

13. The implantable stimulator of claim 8 wherein said current monitoring means comprises a current-to-voltage converter means for generating a current-indicating voltage $v_i$ that varies as a function of the measured average current flowing through the electrical current path.

14. The implantable stimulator of claim 13 wherein said current-to-voltage converter means comprises two current mirror circuits, a first of which generates a voltage $v_1$ that varies as a function of the measured average current flowing in one direction through the electrical current path, and a second of which generates a voltage $v_2$ that varies as a function of the measured average current flowing in the other direction through the electrical current path.

15. The implantable stimulator of claim 14 wherein said current-to-voltage converter means includes means for generating a signal Wn which specifies a particular current polarity for the current-indicating voltage $v_i$.

16. The implantable stimulator of claim 3 wherein said first and second circuit means are realized using CMOS transistors configured to function as prescribed circuit elements on the same semiconductor chip.

17. The implantable stimulator of claim 1 wherein said second circuit means comprises electronic circuit control means, further comprising a plurality of circuit elements that do not include a coupling capacitor or a coupling transformer in the electrical current path, for preventing a stimulation current pulse from being applied through said electrical current path unless said stimulation current pulse comprises a biphasic current pulse.

18. The implantable stimulator of claim 17 wherein said electronic circuit control means comprises:

current monitoring means for monitoring the amplitude and polarity of a stimulation current pulse flowing through said electrical current path as a function of time; and comparison means for comparing the current monitored by the current monitoring means with a reference value, and for preventing further current flow in the electrical current path in the event the current monitored by the current monitoring means is not a biphasic current pulse.

19. The implantable stimulator of claim 18 wherein said current monitoring means comprises a current-to-voltage converter means for generating a current-indicating voltage $v_i(t)$ that varies as a function of the measured current flowing through the electrical current path over time, and means for generating a reference voltage $v_{REF}(t)$; and wherein said comparison means comprises voltage comparator means for comparing the voltage $v_i(t)$ with the reference voltage $v_{REF}(t)$, and switch means for disrupting the electrical current path whenever $v_i(t)$ differs from $V_{REF}(t)$ by more than a prescribed amount.

20. The implantable stimulator of claim 1 wherein said first circuit means generates a biphasic current stimulation pulse, and wherein said second circuit means comprises electronic circuit control means for cancelling dc current flow in the electrical current path.

21. The implantable stimulator of claim 20 wherein said means for cancelling dc current flow comprises:

means for sensing current flow in the electrical current path and generating a first signal representative of the sensed current flow;

means for integrating the first signal and generating a second signal that comprises the integrated first signal, and wherein said means for integrating uses a time constant that is much longer than the biphasic current stimulation current pulse so that the integrator only responds to average dc current; and transconductance amplifier means for converting the second signal to a second current and for injecting the second current back into the electrical current path.

22. The implantable stimulator of claim 1 wherein said first circuit means generates a biphasic current stimulation pulse, and wherein said second circuit means comprises means for measuring an average dc current and electronic circuit control means for blocking dc current flow through the electrical current path whenever the average dc current exceeds a prescribed threshold.

23. The implantable stimulator of claim 22 wherein said means for blocking dc current flow comprises:

means for sensing current flow in the electrical current path and generating a first signal representative of the sensed current flow;

means for integrating the first signal and generating a second signal that comprises the integrated first signal, and wherein said means for integrating uses a time constant that is much longer than the biphasic current stimulation current pulse so that the integrator only responds to average dc current;

means for comparing the second signal to the prescribed threshold and generating a first latch signal in the event the second signal exceeds the prescribed threshold; and switch means for disrupting the electrical current path in response to the first latch signal.

24. The implantable stimulator of claim 23 wherein said means for comparing comprises means for comparing the second signal to a positive threshold and a negative threshold, and for generating the first latch signal in the event that the second signal exceeds either the positive threshold or the negative threshold.

25. An implantable living tissue stimulator comprising:

a biphasic current pulse generator; and output circuit means for receiving a biphasic current pulse generated by the biphasic current pulse generator and directing such biphasic current pulse along an electrical current path to a selected pair of a plurality of output terminals;

said output circuit means comprising prevention means for preventing an average dc current flow through the electrical current path, said prevention means comprising a plurality of circuit elements that do not include a coupling capacitor in the electrical current path.

26. The implantable stimulator of claim 25 wherein said prevention means comprises means for cancelling dc current flow in the electrical current path.

27. The implantable stimulator of claim 26 wherein said means for cancelling dc current flow in the electrical current path comprises:

means for sensing current flow in the electrical current path and generating a first signal representative of the sensed current flow;

means for integrating the first signal and generating a second signal that comprises the integrated first signal, and wherein said means for integrating uses a time constant that is much longer than the biphasic current stimulation current pulse, whereby the integrator only responds to average dc current; and transconductance amplifier means for converting the second signal to a second current and for injecting the second current back into the electrical current path.

28. The implantable stimulator of claim 25 wherein said prevention means comprises means for cutting off the dc current flow through the electrical current path whenever the dc current exceeds a prescribed threshold.

29. The implantable stimulator of claim 28 wherein said means for cutting off the dc current flow comprises:

means for sensing current flow in the electrical current path and generating a first signal representative of the sensed current flow;

means for integrating the first signal and generating a second signal that comprises the integrated first signal, and wherein said means for integrating uses a time constant that is much longer than the biphasic current stimulation current pulse, whereby the integrator only responds to average dc current;

means for comparing the second signal to the prescribed threshold and generating a first latch signal in the event the second signal exceeds the prescribed threshold; and switch means for disrupting the electrical current path in response to the first latch signal.

30. An implantable living tissue stimulator comprising:

biphasic current pulse generator means for generating a series of biphasic current pulses;

output circuit means for receiving a biphasic current pulse generated by the biphasic current pulse generator means and directing such biphasic current pulse along an electrical current path to a selected pair of a plurality of output terminals;

an electrode array comprising a plurality of electrodes, each electrode of said plurality of electrodes being connected to one of the plurality of output terminals, a selected pair of said plurality of electrodes thereby having the biphasic current pulse applied thereto; and means for preventing dc current flow, without output coupling capacitors or output coupling transformers, through the selected pair of said plurality of electrodes of said electrode array.

31. The stimulator as set forth in claim 30 wherein the means for preventing dc current flow through the selected pair of said plurality of electrodes of said electrode array comprises electronic circuit means inserted into the electrical current path between the biphasic current pulse generator and the selected pair of the plurality of output terminals that simulates a coupling capacitor.

32. The stimulator as set forth in claim 30 wherein the means for preventing dc current flow through the selected pair of said plurality of electrodes of said electrode array comprises electronic circuit means inserted into the electrical current path between the biphasic current pulse generator and the selected pair of the plurality of output terminals that cancels average dc current flow in the electrical current path.

33. The stimulator as set forth in claim 30 wherein the means for preventing dc current flow through the selected pair of said plurality of electrodes of said electrode array comprises electronic circuit means inserted into the electrical current path between the biphasic current pulse generator and the selected pair of the plurality of output terminals for disrupting the dc current flow in the electrical current path whenever the amplitude of the dc current exceeds a prescribed threshold.

34. The stimulator as set forth in claim 30 wherein the means for preventing dc current flow through the selected pair of said plurality of electrodes comprises an electrode-tissue interface capacitance, and wherein each electrode of the selected pair of electrodes has an oxide layer thereon, and further wherein each electrode of the selected pair of electrodes comprises a plate of the electrode-tissue interface capacitance, with the oxide layer on each electrode functioning as a dielectric material for the electrode-tissue interface capacitance.

35. The stimulator as set forth in claim 34 wherein the electrode means comprises means for making said electrodes from a sintered anodizable material.

36. The stimulator as set forth in claim 35 wherein said sintered anodizable material comprises sintered anodizable tantalum.

37. A method of stimulating living tissue with a stream of biphasic stimulation current pulses while preventing an average dc current flow from flowing through the living tissue, said method comprising:

generating a series of biphasic stimulation current pulses;

applying the series of biphasic stimulation pulses to an electrical current path that includes an electrode pair in contact with the living tissue; and cancelling dc current flow in the electrical current path by:
  sensing any dc current flow in the electrical current path having a time constant associated therewith that is longer than the biphasic stimulation current pulse,
  generating an offsetting current that is equal to but opposite in polarity from the sensed dc current flow, and
  injecting the offsetting current into the electrical current path.

38. A method of stimulating living tissue with a stream of biphasic stimulation current pulses while preventing an average dc current flow from flowing through the living tissue, said method comprising:

generating a series of biphasic stimulation current pulses;

applying the series of biphasic stimulation pulses to an electrical current path that includes an electrode pair in contact with the living tissue; and blocking dc current flow in the electrical current path by:
  sensing any dc current flow in the electrical current path having a time constant associated therewith that is longer than the biphasic stimulation current pulse,
  comparing the sensed dc current to a prescribed threshold level, and
  disrupting the electrical current path to the tissue whenever the sensed dc current exceeds the prescribed threshold level.

* * * * *